US009909409B2

(12) United States Patent
Bryndzia et al.

(10) Patent No.: US 9,909,409 B2
(45) Date of Patent: Mar. 6, 2018

(54) METHODS FOR ESTIMATING RESOURCE DENSITY USING RAMAN SPECTROSCOPY OF INCLUSIONS IN SHALE RESOURCE PLAYS

(71) Applicant: Shell Oil Company, Houston, TX (US)

(72) Inventors: Lubomyr Taras Bryndzia, Houston, TX (US); Saad Jamil Saleh, Sugar Land, TX (US); Calum Ian Macaulay, Houston, TX (US); Neil Robert Braunsdorf, Sugar Land, TX (US); Theodericus Johannes Henricus Smit, Rijswijk (NL); Ronny Hofmann, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 599 days.

(21) Appl. No.: 14/501,363

(22) Filed: Sep. 30, 2014

(65) Prior Publication Data

US 2015/0090443 A1 Apr. 2, 2015

Related U.S. Application Data

(60) Provisional application No. 61/885,070, filed on Oct. 1, 2013.

(51) Int. Cl.
*E21B 47/06* (2012.01)
*G01N 33/24* (2006.01)

(52) U.S. Cl.
CPC ........... *E21B 47/06* (2013.01); *G01N 33/241* (2013.01)

(58) Field of Classification Search
CPC .................. E21B 47/06; G01N 33/241
See application file for complete search history.

(56) References Cited

U.S. PATENT DOCUMENTS

| 4,715,711 A | 12/1987 | Dunn |
| 5,498,960 A | 3/1996 | Vinegar et al. |
| 6,393,906 B1 * | 5/2002 | Vityk ...................... E21B 49/00 166/269 |

(Continued)

FOREIGN PATENT DOCUMENTS

| CN | 1043564 A | 7/1990 |
| CN | 1161085 A | 10/1997 |

(Continued)

OTHER PUBLICATIONS

Dutta, Nader C., et al.: Estimation of formation fluid pressure using high-resolution velocity from inversion of seismic data and a rock physics model based on compaction and burial diagenesis of shales, The Leading Edge, vol. 25, No. 12, Dec. 31, 2006, pp. 1528-1539, XP055186913.

(Continued)

*Primary Examiner* — Bryan Bui

(57) ABSTRACT

A method of determining the in situ pressure of a light hydrocarbon in a shale source rock formation comprising: providing an inclusion comprising the light hydrocarbon trapped within the inclusion; using Raman spectroscopy to determine the density and composition of the light hydrocarbon trapped within the inclusion; and calculating a pressure of the light hydrocarbon in the shale source rock formation based upon the density and composition of the light hydrocarbon trapped within the inclusion.

6 Claims, 3 Drawing Sheets

(56) References Cited

U.S. PATENT DOCUMENTS

| | | |
|---|---|---|
| 2003/0048450 A1 | 3/2003 | Pope et al. |
| 2004/0061858 A1 | 4/2004 | Pope et al. |
| 2011/0036146 A1 | 2/2011 | Pope et al. |
| 2012/0312530 A1 | 12/2012 | Pope et al. |

FOREIGN PATENT DOCUMENTS

| | | |
|---|---|---|
| CN | 103245588 A | 8/2013 |
| WO | 2011077271 A1 | 6/2011 |

OTHER PUBLICATIONS

Xiao, Yitian, et al.: Evaluation in Data Rich Fayetteville Shale Gas Plays—Integrating Physics—based Reservoir Simulations with Data Driven Approaches for Uncertainty Reduction Introduction, Proceedings of the 2012 International Petroleum Technology Conference, Feb. 9, 2012, pp. 1-19, SXP055187088.

Liu, Dehan, et al.: Muliple types of high density methane inclusions and their relationships with exploration and assessment of oil-cracked gas and shale gas discovered in NE Sichuan, Earth Science Frontiers, vol. 20 (1), pp. 64-71, 2013 XP055150101.

Liu, Dehan, et al.: Muliple types of high density methane inclusions and their relationships with exploration and assessment of oil-cracked gas and shale gas discovered in NE Sichuan, English translation, Earth Science Frontiers, vol. 20 (1), pp. 1-9, XP055151364.

Lu, Wanjun, et al.: A unified equation for calculating methane vapor pressures in the CH4-H2O system with measured Raman shifts, Geochimica et Cosmochimica ACTA, Pergamon Press, NY, vol. 71, No. 16, pp. 3969-3978, 2007, XP022184322.

International Search Report dated Jan. 20, 2015 for PCT/US2014/58163 filed Sep. 30, 2014.

* cited by examiner

METHODS FOR ESTIMATING RESOURCE DENSITY USING RAMAN SPECTROSCOPY OF INCLUSIONS IN SHALE RESOURCE PLAYS

RELATED CASES

This application claims the benefit of U.S. Provisional Application No. 61/885,070, filed on Oct. 1, 2013, which is incorporated herein by reference.

BACKGROUND

The present disclosure relates generally to methods for estimating the in situ density of light hydrocarbons. More specifically, in certain embodiments, the present disclosure relates to methods for estimating in situ density of light hydrocarbons in shale source rock vein and matrix minerals using Raman spectroscopy and associated methods.

One of the objectives of an exploration and appraisal campaign in unconventional shale gas and liquid rich shale plays is to "sweet spot" the acreage in terms of potential estimated ultimate recovery (EUR). Sweet spotting is a term used to refer to the identification of the top quartile wells in a given production zone. This is often difficult to do in the absence of reliable production data. Estimating EUR in shale gas formations is especially challenging since EUR is a dynamic production metric while all other rock properties being measured are static in-situ properties. The relationship between these different states is not intuitive and presently poorly understood. In order to successfully sweet spot an unconventional shale source rock play, an estimate of the mass of light hydrocarbon per volume of source rock (i.e. the in situ density of light hydrocarbon) is required.

It is desirable to develop a method of determining in situ density and pressure of light hydrocarbons in a gas-bearing shale source rock in order to develop accurate EUR maps and identify sweet spots in the shale source rock formations.

SUMMARY

The present disclosure relates generally to methods for estimating the in situ density of light hydrocarbons. More specifically, in certain embodiments the present disclosure relates to methods for estimating in situ density of light hydrocarbons in shale source rock vein and matrix minerals using Raman spectroscopy and associated methods.

In one embodiment, the present disclosure provides a method of determining the in situ pressure of a light hydrocarbon in a shale source rock formation comprising: providing an inclusion comprising the light hydrocarbon trapped within the inclusion; using Raman spectroscopy to determine the density and composition of the light hydrocarbon trapped within the inclusion; and calculating a pressure of the light hydrocarbon in the shale source rock formation based upon the density and composition of the light hydrocarbon trapped within the inclusion.

In another embodiment, the present disclosure provides a method of evaluating a shale source rock formation comprising: providing inclusions from the shale source rock formation, wherein each inclusion comprises a light hydrocarbon trapped within the inclusion; determining in situ pressures and densities of the light hydrocarbon within the shale source rock formation utilizing Raman analyses of the light hydrocarbon trapped within inclusions; and producing a map of the spatial and vertical variations of the in situ pressures and densities of the light hydrocarbon in the shale source rock formation.

In another embodiment, the present disclosure provides a method of evaluating a shale source rock formation comprising: providing inclusions from the shale source rock formation, wherein each inclusion comprises a light hydrocarbon trapped within the inclusion; determining in situ pressures and densities of the light hydrocarbon utilizing Raman analyses of the light hydrocarbon trapped within inclusions; producing a map of spatial and vertical variations of proxies for pressure normalized-estimated ultimate recovery; and identifying the areas on the map that correspond to a top quartile for pressure normalized-estimated ultimate recovery.

BRIEF DESCRIPTION OF THE DRAWINGS

A more complete and thorough understanding of the present embodiments and advantages thereof may be acquired by referring to the following description taken in conjunction with the accompanying drawings.

Figure 1:
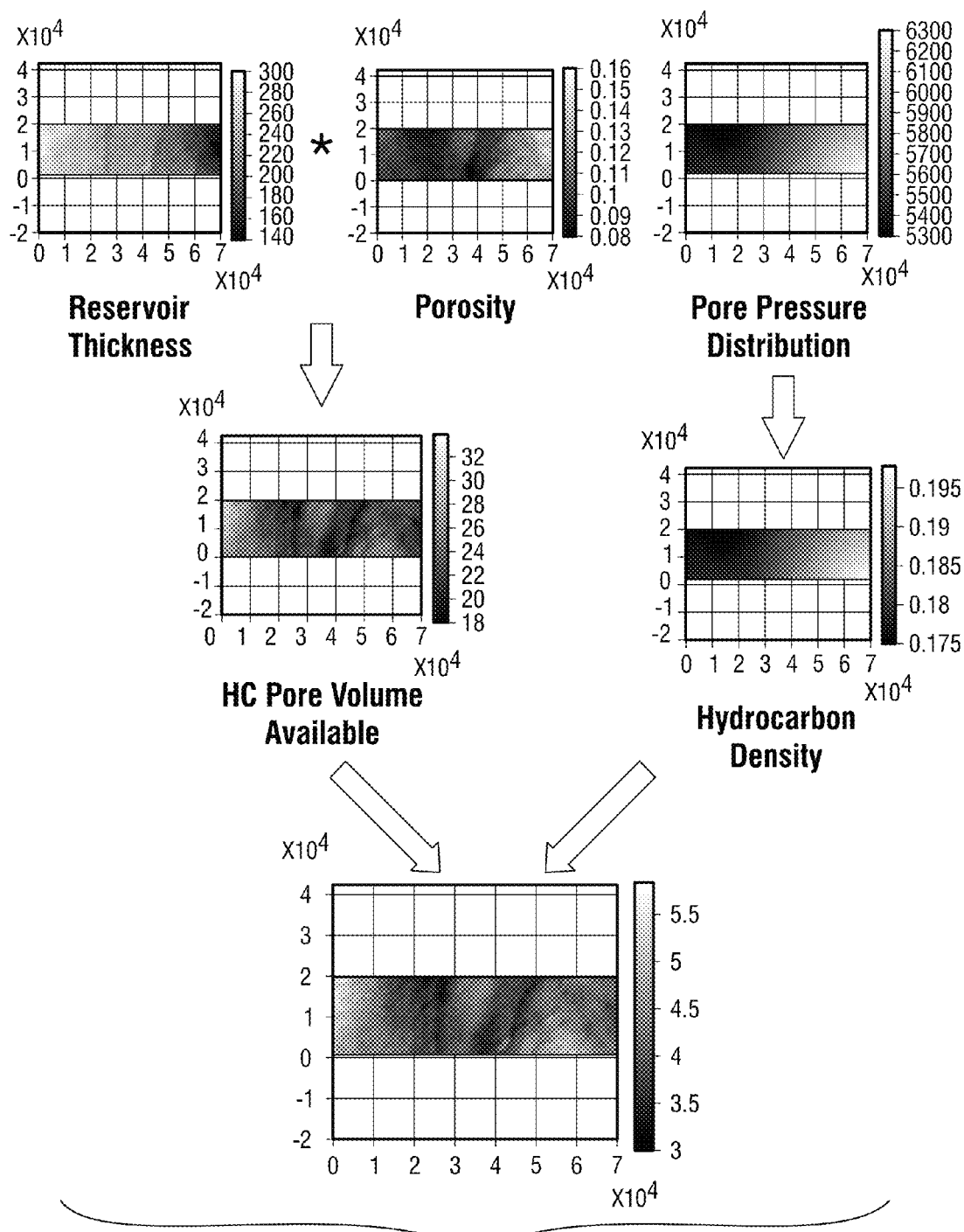
FIG. 1 is an illustration of the convolution of various aerial distributions of reservoir data to create an aerial distribution of hydrocarbon volume and proxy PN-EUR.

The features and advantages of the present disclosure will be readily apparent to those skilled in the art. While numerous changes may be made by those skilled in the art, such changes are within the spirit of the disclosure.

DETAILED DESCRIPTION

The description that follows includes exemplary apparatuses, methods, techniques, and/or instruction sequences that embody techniques of the inventive subject matter. However, it is understood that the described embodiments may be practiced without these specific details.

The present disclosure relates generally to methods for estimating the in situ density of light hydrocarbons. More specifically, in certain embodiments the present disclosure relates to methods for estimating in situ density of light hydrocarbons in shale source rock vein and matrix minerals using Raman spectroscopy and associated methods.

Some desirable attributes of the methods discussed herein are that they are more accurately able to predict areas and volumes of organic rich source rocks with favorable estimated ultimate recovery attributes. By measuring the pressure and density of light gases in an organic-rich shale source rock formation, it is possible to produce more accurate maps of estimated ultimate recovery for sweet spotting purposes than conventional methods. Sweet spotting may be achieved by mapping in two dimensions estimated ultimate recovery data and making a map that then can highlight the most favorable part of a basin/play/prospect for early development based on the spatial distribution of resource density i.e. the density of hydrocarbon per volume of rock.

In certain embodiments, this disclosure outlines methods for evaluating the densities of light hydrocarbons generated by organic rich source rock shale. These methods may be based on the association of light hydrocarbon density trapped as inclusions in shale matrix and vein material within an organic rich shale source rock. The density of the light hydrocarbon may be quantified using a Raman spectroscopic method. A strong correlation between the densities of the light hydrocarbon generated by a shale source rock and estimated ultimate recovery, specifically the pressure normalized-estimated ultimate recovery, has been observed. Because of this correlation, the in situ densities and pressures of the light hydrocarbon at various points in the formation may be inferred from an Equation of State model and the measured density, pressure, and temperature of the light hydrocarbons trapped as inclusions. The in situ densities and pressures may be recognized proxies for pressure normalized-estimated ultimate recovery data that is normally obtained from production data.

In one embodiment, the present disclosure provides a method for estimating the pressure of a light hydrocarbon in a shale source rock formation comprising: providing an inclusion comprising the light hydrocarbon trapped within the inclusion; using Raman spectroscopy to determine the density and composition of the light hydrocarbon trapped within the inclusion; and calculating a pressure of the light hydrocarbon in the shale source rock formation based upon the density and composition of the light hydrocarbon trapped within the inclusion.

In certain embodiments, the light hydrocarbon may be any hydrocarbon which is a gas at standard pressure and temperature conditions. Suitable examples of light hydrocarbons include methane, ethane, propane, butane, pentane, or any combination thereof.

In certain embodiments, the shale source rock formation may be a recognized source rock based on its total organic carbon (TOC) content. In other embodiments, the shale source rock formation may be an organic-rich shale source rock formation comprising a natural gas liquid resource in which a light hydrocarbon may not be the dominant hydrocarbon species. Regardless of the particular type of shale source rock formation, the total pressure of the light hydrocarbons at a particular location in the shale source rock formation may be a summation of all of the partial pressures of gas components present and individual species partial pressures at that particular location and thus may still serve as a valid proxy for the pressure normalized-estimated ultimate recovery of any of the component hydrocarbon species present in the formation of interest.

In certain embodiments, the inclusion may be an inclusion found in a rotary core or a side wall core from the well bore of the shale source rock formation. The inclusion may be disposed in a mineral phase that is amenable to analysis using Raman spectroscopic methods. Examples of suitable mineral phases include crystals of quartz, calcite, anhydrite, barite, gypsum, albite, and other members of the feldspar group of minerals.

In certain embodiments, the inclusion may be single phase containing only light hydrocarbons. In other embodiments, the inclusion may be multiphase containing liquid water, carbon dioxide, and light hydrocarbon and potentially other species stable within the C—O—H—S—N system generated as products of the maturation of the given organic rich shale source rock. The inclusion may also contain different proportions of gas to liquid and also daughter minerals that are stable in the chemical microcosm of the fluid inclusion formed during the burial and uplift history of a given shale source rock formation.

In certain embodiments, the inclusions may first be prepared before Raman spectroscopy is performed. The inclusions may be prepared by using conventional techniques used in the preparation of fluid inclusion wafers. For example, in certain embodiments, 100 micron thick wafers may be prepared to have a surface polish quality such that the Raman incident laser beam can interact with the trapped hydrocarbon components of the inclusion, return a signal that is then measured as a characteristic peak shift specific to certain types of characteristic vibrational modes of molecular bonds, suitable for quantification relative to a reference peak shift for a specific C bond in a hydrocarbon molecule.

In certain embodiments, Raman spectroscopy may be performed by focusing a laser beam into the inclusion in order to excite a reflected photon beam that is captured as a series of spectral lines corresponding to characteristic peak shifts of vibrational modes of different C bonds that may are diagnostic of the hydrocarbons trapped in the inclusions. The Raman spectra may be collected at ambient laboratory conditions during which careful records of temperature and peak shifts may be recorded. In order to access the multi micron dimension of average fluid inclusions, in certain embodiments, the Raman spectroscopy may be micro Laser Raman Spectroscopy.

In certain embodiments, a laser light source with different wavelengths may be used, depending on the composition of the light hydrocarbons trapped in the inclusion. Briefly, a low energy laser beam may be used to excite different modes of bond vibrations in molecular moieties of the light hydrocarbons trapped in the inclusion. Thus, the characteristic peak shift of the light hydrocarbon molecule of interest in the inclusion may be obtained. This peak shift data may then be compared to prior calibration peak shift data to determine the density of the trapped light hydrocarbons of a particular composition.

In certain embodiments, the pressure of the light hydrocarbon in the shale source rock formation may be calculated based upon the density and composition of the light hydrocarbon trapped in the inclusion. For example, an Equation of State model may be used to calculate the pressure of the light hydrocarbon at the location from where the inclusion was sampled. In certain embodiments, commercially available PVT simulation software packages may be used to calculate the pressure of the light hydrocarbon based upon the density and composition of the light hydrocarbon trapped in the inclusion.

In embodiments where the shale source rock formation contains only one type of light hydrocarbons (e.g. only methane) a single Equation of State model for that light hydrocarbon may be used to calculate the pressure in the formation at the location where the inclusion was sampled. In embodiments where the shale source rock formation contains a mixture of light hydrocarbons or other gases, other more suitable Equations of State for mixtures may be used to calculate the partial pressure of each light hydrocarbon or gas and the overall pressure of the mixture. Conversely, a single Equation of State model may be used for mixtures of gases, requiring only the use of thermodynamically established mixing laws for the different components comprising the gas phase.

The variables in the particular Equation of State used to calculate the pressure in the formation may be obtained in a variety of ways.

Temperature may be determined from fluid inclusion thermometry and inferences drawn from the homogenization temperatures at which two phase liquid and gas inclusions are observed to homogenize into a single phase on heating under a calibrated micro heating stage.

Density may be defined as the mass of gas component divided by its volume. The inclusion volume may be assumed to remain constant between ambient laboratory conditions at which the Raman data are collected and the temperature at which the original fluid inclusion was trapped. By measuring density of the gas component directly using Raman spectroscopy, the mass/volume relationship implied by certaom Equation of State models may be satisfied.

Once the temperature at which the inclusion was trapped is known and its density at ambient conditions is measured, the pressure at which the light hydrocarbon was trapped may be solved iteratively. The iterative procedure may involve determining the pressure that satisfies density at the fluid inclusion trapping temperature, based on certain assumptions about the average bulk composition of the gaseous phase present at the time of trapping. The assumptions about the average bulk composition of the gaseous phase present at the time of trapping may include the particular mole fractions of gas phases present and whether or not the gas phase is water saturated.

Thus, by using the methods discussed above, the pressure and density of a light hydrocarbon in a formation at the location where the inclusion was formed may be estimated.

In certain embodiments, the present disclosure provides a method of evaluating a shale source rock formation comprising: providing inclusions from the shale source rock formation, wherein each inclusion comprises a light hydrocarbon trapped within the inclusion; determining in situ densities and pressures of the light hydrocarbon within the shale source rock formation utilizing Raman analyses of the light hydrocarbon trapped within inclusions; and producing a map of the spatial and vertical variations of the in situ pressures of the light hydrocarbon in the shale source rock formation.

In certain embodiments, inclusions may be obtained from multiple locations within the shale source rock formation and from several different well locations. Raman analyses on each of these inclusions may be performed, and estimates for pressures and densities of light hydrocarbons at multiple locations in the shale source rock formation may be made. The pressures and densities of the light hydrocarbons at locations not measured may be estimated using conventional interpolation and/or extrapolation techniques. Using these estimates, a map depicting the spatial and vertical variations of the pressures of the light hydrocarbons may be produced.

In certain embodiments, a map depicting the spatial and vertical variations of the pressures of the light hydrocarbons may be produced by performing diagnostic formation integrity tests plotting the results of those tests.

In certain embodiments, the present disclosure provides a method of evaluating a shale source rock formation comprising: providing inclusions from the shale source rock formation, wherein each inclusion comprises a light hydrocarbon trapped within the inclusion; determining in situ pressures and densities of the light hydrocarbon utilizing a Raman analysis of the light hydrocarbon trapped within inclusions; producing a map of spatial and vertical variations of proxies for pressure normalized-estimated ultimate recovery; and identifying the areas on the map that correspond to a top quartile for pressure normalized-estimated ultimate recovery.

In certain embodiments, the map predicting the spatial and vertical variation of pressure normalized-estimated ultimate recovery may be produced relying solely on the data obtained from any of the methods discussed above. The in situ pressures of the light hydrocarbons may then be mapped and the areas with top quartile potential may be identified. Typically, the best producing intervals of the formation correlate with the pressure normalized-estimated ultimate recovery. Thus, in situ density and/or pressure may be used as a proxy for pressure normalized-estimated ultimate recovery.

In certain embodiments, producing the map of the spatial and vertical variation of proxies for pressure normalized-estimated ultimate recovery may comprise using the calculated partial pressures of various light hydrocarbon components as proxies for pressure normalized-estimated ultimate recovery at each of those locations and preparing a map based upon these proxies. In certain embodiments, these proxies may also be calculated based upon formation properties such as Total Organic Carbon, porosity, gas composition, and pressure, temperature, and volume properties of the light hydrocarbons.

The formation properties may be determined in a variety of ways. In certain embodiments, a variety of these formation properties, for example, gas composition, pressure, temperature, and/or volume, may be determined using any of the methods described above.

In certain embodiments, other formation properties at multiple locations may be calculated using seismic data such as acoustic and elastic impendence of the subsurface formation using an inversion algorithm. An example of a seismic inversion algorithm may include the following steps: (1) seed an initial subsurface model with an initial estimate of the subsurface acoustic and elastic impedances, (2) generate a synthetic systemic response based on the initial estimate using a forward modeling algorithm that simulates the dependence of seismic properties on variation in acoustic and elastic impedances, and (3) compare the synthetic data with the actual seismic data. When comparing the synthetic data with the actual seismic data, if the error is acceptably small the initial estimate may be accepted as the final result. This model may then be used to produce the pressure normalized-estimated ultimate recovery maps. On the other hand, if the error is unacceptably large, the subsurface model may be perturbed in a manner that can improve agreement with the measured data and then steps (2) and (3) may be repeated until the error is acceptably small and convergence is obtained.

After an agreement of synthetic data and field data is reached, the inverted seismic properties may be used to calculate formation properties. Several additional calibration steps may be involved to determine formation properties for unconventional reservoirs compared to conventional formations. The acoustic properties of the organic matter and kerogen may have to be established by using methods such as nanoindentation of the organic matter in order to estimate mechanical and elastic properties. With these properties established, the inverted acoustic properties may then be used to estimate to volume of organic matter and bulk density of the formation. A map of the thickness of the reservoir interval in the area of interest may then be generated using these results.

To convert a bulk density into porosity, the density of the organic matter and/or kerogen may need to be known. The maturity of the kerogen may be determined by using Raman measurement of solid organic matter and then estimating a ratio of the D5/G peak ratio, where D5 and G refer to characteristic Raman peaks of organic components in the solid organic matter, specifically the aliphatic C—C stretch vibrational mode (D5) and the bulk aromatic or grapheme like component (G). The grain density of the organic matter may then be estimated based on the maturity of the kerogen and a proprietary correlation between maturity and the grain density of solid organic matter. Using the volume and density of the organic matter and the bulk density of the rock mineral matrix, the porosity of the formation may then be estimated. A map of the average porosity of the reservoir interval in the area of interest may then be generated using these results.

The maps of the thickness of the reservoir interval and the average porosity of the reservoir interval may then be convolved to generate a map of the distribution of the potential pore space volume of the reservoir interval in the area of interest. The map depicting the spatial and vertical variations of the partial pressures of the light hydrocarbons may then be convolved with the map of the distribution of the potential pore space volume to produce a pressure normalized-estimated ultimate recovery map. Using this data, a map that predicts the spatial and vertical variations of estimated ultimate recovery may be produced and the areas on that map may then be identified as having the potential to be top quartile candidates for development. FIG. 1 provides an illustration of the convolution of these maps. As can be seen in FIG. 1, the lighter colored areas of each map correspond to higher values of thickness, porosity, pore space, partial pressure, hydrocarbon density, and estimated ultimate recovery.

To facilitate a better understanding of the present invention, the following examples of certain aspects of some embodiments are given. In no way should the following examples be read to limit, or define, the scope of the invention.

EXAMPLES

Example 1

Fluid inclusion sections were prepared from pieces of vein and core material containing calcite, quartz, barite, and anhydrite. Fluid inclusion wafers were prepared using standard industry methods, resulting in polished thin sections suitable for petrographic examination and characterization of fluid inclusion types.

Thermometric studies were conducted involving measuring temperatures of homogenization of the aqueous inclusions, thereby defining the temperature at which the inclusions formed. Freezing point temperatures were then measured in order to estimate the average salinity of the coexisting brines, which are an established function of total dissolved salt in the aqueous phase of the brine. During petrographic examination, liquid petroleum and gas inclusions were also be identified by routine examination under Ultraviolet light. Liquid petroleum inclusions may be recognized by their blue fluorescence, while hydrocarbon gas may appear isotropic under plain white light and do not fluoresce under Ultraviolet light.

Figure 2A:
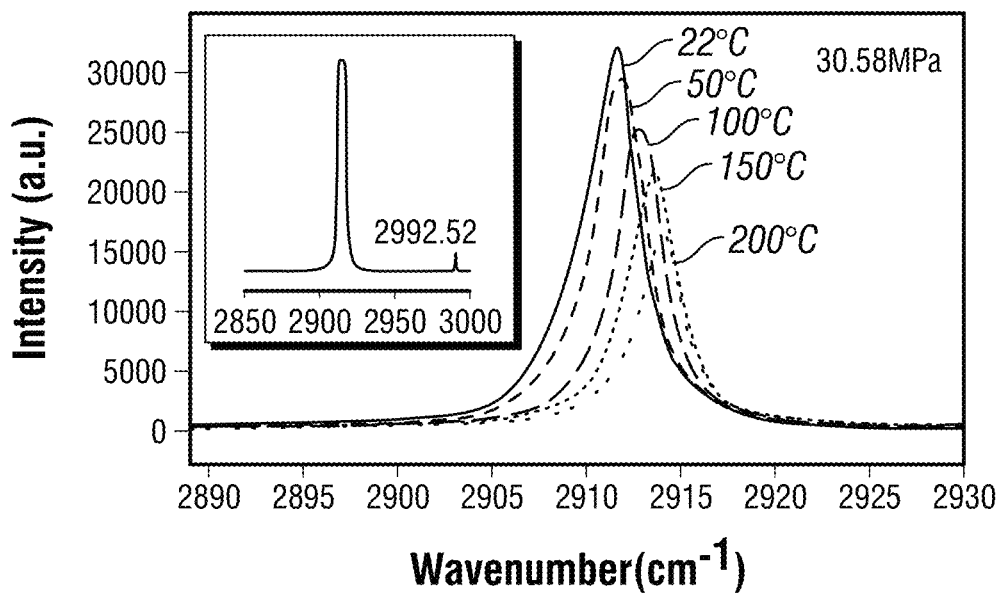
FIGS. 2A-2C are charts depicting the relationship between pressure and concentration of light hydrocarbons and Raman peak shift data.
Figure 2B:
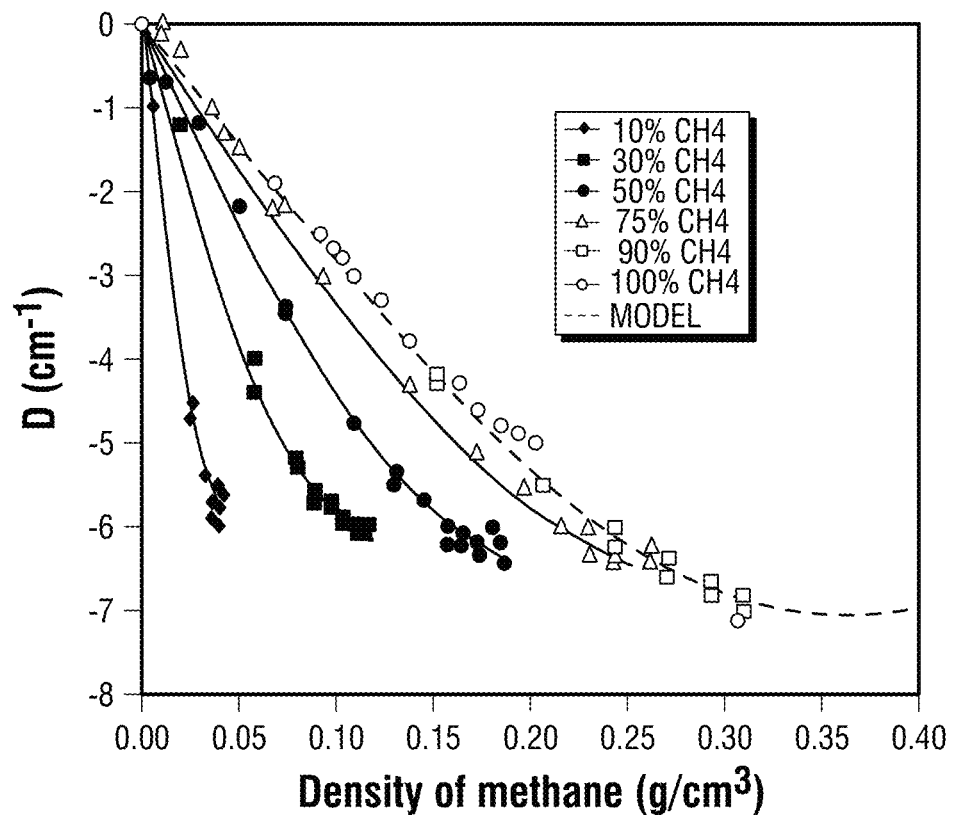
Figure 2C:
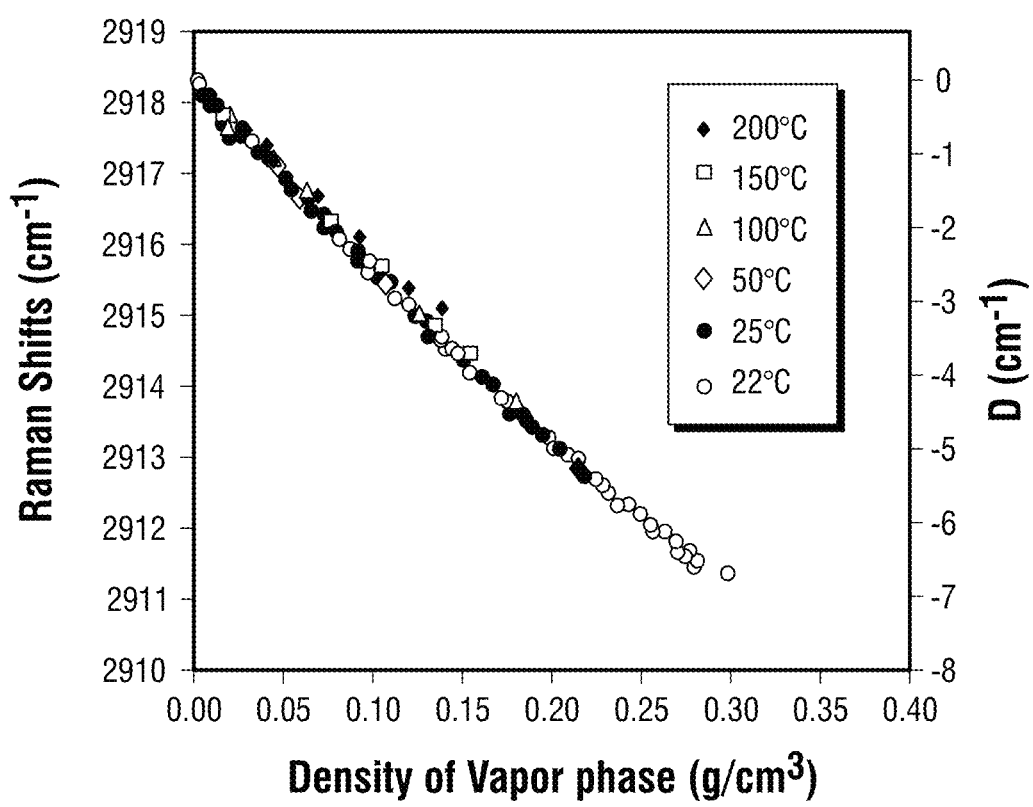

FIG. 2A shows the sensitivity of the characteristic Raman peak shift of CH4 as a function of temperature, at a constant pressure of 30.58 MPa. FIG. 2B shows the relationship between methane pressure and D (cm−1) at room temperature, where D is the Delta between the measured peak shift of methane trapped in the inclusion and an "intercept" value, based on a calibration of the methane peak shift at zero pressure for the Raman instrument configuration used to measure the Raman peak shifts in inclusions. FIG. 2C shows the model relationships between Raman peak shift, D (cm−1) and density of the vapor phase, as a function of temperature.

Using Raman peak shifts measured in methane-bearing fluid inclusions, in situ methane density may be calculated using an Equation of State. Table 1 below illustrates the result of such calculations.

TABLE 1

| Sample | Temp (° C.) | Peak shift (cm$^{-1}$) | Intercept (cm$^{-1}$) | D (cm$^{-1}$) | Density of $CH_4$ ($CH_4$—$CO_2$—$H_2O$) | At 25° C. P $CH_4$ MPa | At FI Temperature P $CH_4$ MPa | psi |
|---|---|---|---|---|---|---|---|---|
| 11 | 140 | 2910.5 | 2917.2 | −6.7 | 0.2758 | 54.1 | 74.50 | 10305 |
| 21 | 160 | 2910.8 | 2917.2 | −6.4 | 0.2611 | 46.0 | 72.64 | 10535 |
| 29 | 160 | 2910.4 | 2917.2 | −6.8 | 0.2808 | 57.2 | 83.00 | 12037 |
| SU | 150 | 2910.9 | 2917.2 | −6.3 | 0.2563 | 43.7 | 67.80 | 9833 |

($CH_4$:$CO_2$ (94:6)-$H_2O$)

In order to convert the peak shift for methane from the micro laser Raman measurements in Table 1, some assumptions as to the composition of the vapor phase in the samples was required. For this Example, a composition production gas, namely 94 mole % CH4 and 6 mole % CO2, saturated with water vapor at in situ conditions was used.

The methane pressures in Table 1 were estimated using an Equation of State (EOS) calculator for CH4-CO2 mixtures saturated with water vapor (PVTsim, a commercially available PVT simulation software package). In situ methane pressures were obtained by iterative simulation until the measured vapor density at 25° C. was matched at the fluid inclusion temperatures. These methane pressures are in the last column of Table 1.

The Raman data shows that the in situ methane pressure in Sample SU was lower than in the other samples. Sample SU was from a well with reported pressure normalized-estimated ultimate recoveries that have generally been very disappointing. It was speculated that the poor pressure normalized-estimated ultimate recoveries may be related to lower in situ methane density, which is reflected in the pressure estimates.

While the embodiments are described with reference to various implementations and exploitations, it will be understood that these embodiments are illustrative and that the scope of the inventive subject matter is not limited to them. Many variations, modifications, additions and improvements are possible.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A method comprising:
   providing inclusions from the shale source rock formation, wherein each inclusion comprises a light hydrocarbon trapped within the inclusion;
   determining in situ pressures and densities of the light hydrocarbon within the shale source rock formation utilizing Raman analyses of the light hydrocarbon trapped within inclusions wherein said Raman analyses comprises obtaining a characteristic peak shift of the light hydrocarbon trapped within the inclusion and comparing this peak shift to prior calibration peak shift data to determine the density of the trapped light hydrocarbons of a particular composition;
   producing a map of spatial and vertical variations of the in situ pressures and densities of the light hydrocarbon in the shale source rock formation highlighting most favorable parts of the shale rock formation for early development; and
   developing the most favorable parts of the shale rock formation.

2. The method of claim 1, wherein the light hydrocarbon comprises methane, ethane, propane butane, or any combination thereof.

3. The method of claim 1, wherein the inclusion is disposed within a rotary core or a sidewall core from a wellbore penetrating the shale source rock formation.

4. The method of claim 1, further comprising preparing the inclusion before using Raman spectroscopy to determine the density and composition of the light hydrocarbon trapped within the inclusion.

5. The method of claim 1, wherein micro Laser Raman spectroscopy is used to determine the density and composition of the light hydrocarbon trapped within the inclusion.

6. The method of claim 1, wherein the pressure of the light hydrocarbon in the shale source rock formation is calculated using an equation of state model.

* * * * *